United States Patent
Hiebert et al.

(10) Patent No.: US 6,535,763 B1
(45) Date of Patent: Mar. 18, 2003

(54) EVENT MARKER ALIGNMENT BY INCLUSION OF EVENT MARKER TRANSMISSION LATENCY IN THE REAL-TIME DATA STREAM

(75) Inventors: James F. W. Hiebert, St. Paul; Allan T. Koshiol, Lino Lakes; Howard D. Simms, Jr., Oakdale, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/382,154

(22) Filed: Aug. 22, 1999

(51) Int. Cl.$^7$ ................................................. A61N 1/37
(52) U.S. Cl. ...................................................... 607/32
(58) Field of Search ....................... 607/32, 5; 600/510

(56) References Cited

U.S. PATENT DOCUMENTS

| | | | |
|---|---|---|---|
| 4,223,678 A | * 9/1980 | Langer et al. | |
| 4,407,288 A | 10/1983 | Langer et al. | 128/419 PG |
| 4,527,567 A | 7/1985 | Fischler et al. | 128/419 PT |
| 4,531,527 A | 7/1985 | Reinhold, Jr. et al. | 128/696 |
| 4,596,255 A | 6/1986 | Snell et al. | 128/697 |
| 4,601,291 A | 7/1986 | Boute et al. | 128/419 |
| 4,791,936 A | 12/1988 | Snell et al. | 128/697 |
| 4,809,697 A | 3/1989 | Causey, III et al. | 128/419 PT |
| 4,944,298 A | 7/1990 | Sholder | 128/419 PG |
| 4,979,506 A | 12/1990 | Silvian | 128/419 PT |
| 5,209,228 A | 5/1993 | Cano et al. | 128/419 PT |
| 5,357,969 A | 10/1994 | Herleikson | 128/696 |
| 5,391,188 A | 2/1995 | Nelson et al. | 607/9 |
| 5,402,794 A | 4/1995 | Wahlstrand et al. | 128/696 |
| 5,404,880 A | 4/1995 | Throne | 128/705 |
| 5,413,594 A | * 5/1995 | Williams | 607/32 |
| 5,417,714 A | 5/1995 | Levine et al. | 607/9 |
| 5,431,692 A | 7/1995 | Hansen et al. | 607/28 |
| 5,476,485 A | 12/1995 | Weinberg et al. | 607/28 |
| 5,511,553 A | 4/1996 | Segalowitz | 128/696 |
| 5,549,654 A | 8/1996 | Powell | 607/32 |
| 5,578,063 A | 11/1996 | Bocek et al. | 607/5 |
| 5,591,214 A | 1/1997 | Lu | 607/9 |
| 5,609,615 A | 3/1997 | Sanders et al. | 607/36 |
| 5,620,472 A | 4/1997 | Rahbari | 607/27 |
| 5,628,776 A | 5/1997 | Paul et al. | 607/119 |
| 5,653,737 A | 8/1997 | van Lake | 607/9 |
| 5,683,431 A | 11/1997 | Wang | 607/28 |
| 5,709,712 A | 1/1998 | Paul et al. | 607/27 |
| 5,732,708 A | * 3/1998 | Nau et al. | |
| 5,759,196 A | 6/1998 | Hess et al. | 607/14 |
| 5,782,890 A | 7/1998 | Wahlstrand et al. | 607/32 |
| 5,792,207 A | 8/1998 | Dietrich | 607/32 |
| 5,814,083 A | 9/1998 | Hess et al. | 607/14 |
| 5,891,178 A | 4/1999 | Mann et al. | 607/27 |
| 5,925,067 A | 7/1999 | Lu | 607/28 |
| 5,974,341 A | 10/1999 | Er et al. | 607/31 |
| 6,243,606 B1 | 6/2001 | Mann et al. | 607/14 |
| 6,263,244 B1 | 7/2001 | Mann et al. | 607/28 |
| 6,311,089 B1 | 10/2001 | Mann et al. | 607/30 |

FOREIGN PATENT DOCUMENTS

EP    0850661    7/1998

OTHER PUBLICATIONS

Tanenbaum, A.S., *Computer Networks*, Prentice–Hall, Inc., Englewood Cliffs, NJ, pp. 125–128, (1981).

* cited by examiner

*Primary Examiner*—Scott M. Getzow
(74) *Attorney, Agent, or Firm*—Schwegman Lundberg Woessner & Kluth, P.A.

(57) ABSTRACT

A cardiac rhythm management system transmits event markers from an implantable device to a remote user interface such as an external programmer. The event markers include timestamp information. A printed/displayed event marker representation is aligned to a printed/displayed heart signal representation based at least in part on the timestamp information. Proper alignment of the printed/displayed heart signal representation to the printed/displayed event marker and proper alignment of the printed/displayed event markers with respect to each other, provides more accurate diagnostic information to the caregiver. This assists the caregiver in using the cardiac rhythm management system to provide a patient with proper cardiac rhythm management therapy.

40 Claims, 8 Drawing Sheets

EVENT MARKER ALIGNMENT BY INCLUSION OF EVENT MARKER TRANSMISSION LATENCY IN THE REAL-TIME DATA STREAM

TECHNICAL FIELD

The present system relates generally to event marker alignment by inclusion of event marker transmission latency in the real-time data stream and particularly, but not by way of limitation, to the same for use in a cardiac rhythm management system.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Anti-arrhythmic drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Portions of such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a defibrillation countershock. The counter-shock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by cardiac rhythm management systems is in providing diagnostic data to the physician or other caregiver to assist in determining the efficacy of therapy being delivered by an implanted cardiac rhythm management device. Such diagnostic data is typically displayed on the screen display and/or recorded on a strip chart recording, each of which is provided by a user interface portion of the cardiac rhythm management system, such as a programmer. The programmer is external to the patient and therefore is remote from the implanted cardiac rhythm management device.

Displayed diagnostic data may include, among other things, one or more representations of intrinsic electrical signals produced by the heart, which are referred to as "cardiac signals " or "heart signals." Such cardiac signals include, among other things, electrical depolarizations associated with heart chamber contractions and electrical regularizations associated with heart chamber expansions. Decisions regarding the delivery and/or withholding of cardiac rhythm management therapy are often based at least in part on information included within such cardiac signals. Moreover, cardiac signals may include information indicating the efficacy of therapy that has already been delivered. The cardiac signals obtained by the programmer may include both surface electrocardiogram (ECG) signals, obtained by external ECG skin electrodes yielding ECG signals directly coupled to the programmer via a cable, and electrograms, obtained by implanted electrodes yielding electrogram signals telemetered from the implanted device to the programmer in a real-time data stream.

The real-time data stream from the implanted cardiac rhythm management device to the external programmer may include other data that provides useful diagnostic information to the caregiver. For example, event markers may be displayed on the screen display and/or strip chair recording of the programmer together with the surface ECG and/or electrogram signals. Such event markers annotate the particular times at which certain events associated with the implanted device occur. In one example, representations of such event markers appear on the strip chart recording as upward pointing arrows to indicate the time of occurrence of the marked event, along with a text annotation identifying the type of marker and/or providing other useful information such as the time between successive markers associated with the same chamber of the heart. In this example, "AS" indicates that the associated event marker corresponds to an atrial sense by the implanted device, "AP" indicates that the associated event marker corresponds to an atrial pace by the implanted device. Similarly, "VS" indicates that the associated event marker corresponds to a ventricular sense by the implanted device, "VP" indicates that the associated event marker corresponds to a ventricular pace by the implanted device. Many other marker types exist and are identified by other text annotations. Markers may include additional information. In one example, a corresponding numeral indicates the time interval in milliseconds since the previous event marker in the same chamber. All this information is useful to the caregiver in diagnosing whether the implanted device is providing appropriate cardiac rhythm management therapy.

Implanted cardiac rhythm management devices are designed for low power consumption. This extends the useful life of the battery-powered implanted device before explantation and replacement is required. As a result of power or other limitations, implanted cardiac rhythm management devices typically provide slow telemetry communication of data to the external programmer. In one example, each "frame" of transmitted data includes signal information from first and second (e.g., atrial and ventricular) electrograms as well as marker information from first and second heart chambers (e.g., atrial and ventricular markers).

In this example, each event marker typically includes enough data so that it takes several frames of data to completely transmit the information associated with a single event marker. Thus, a time delay exists between the occurrence of the event and the receipt of the event marker by the external programmer. However, to be useful to the caregiver, the event markers must be displayed on the screen and/or strip chart recording at the proper time relative to the representations of surface ECG and electrogram signals that are being received and displayed without such delay. The surface ECG and electrogram signals may be buffered and delayed by a fixed delay, which is approximately equal to the transmission time between occurrence of the event and receipt of the event marker by the programmer. This allows the external programmer to "align" the event markers in time to the surface ECG and electrogram signals being displayed on the screen and/or strip chart recording. However, if different types of markers are used, and these markers have different transmission times, then buffering the cardiac signals by a fixed delay will not provide proper alignment between the displayed representations of the event markers and cardiac signals, particularly if events occur during the transmission time of a previous event marker associated with the same heart chamber. Thus, there is a need for improved techniques for accurately displaying such diagnostic information for the caregiver.

SUMMARY OF THE INVENTION

This document describes, among other things, portions of a cardiac rhythm management system transmitting event markers from an implantable device to a remote user interface, in which the event markers include timestamp) information upon which alignment of a printed/displayed event marker representation to a printed/displayed heart signal representation is based at least in part. Proper alignment of the printed/displayed heart signal representation to the printed/displayed event marker, and proper alignment of the printed/displayed event markers with respect to each other, provides more accurate diagnostic information to the caregiver. This assists the caregiver in using the cardiac rhythm management system to provide a patient with proper cardiac rhythm management therapy.

In one embodiment, the present cardiac rhythm management system includes an implantable cardiac rhythm management (CRM) device and a user interface (UI), remote from the CRM device. The user interface is adapted to be communicatively coupled to the CRM device for receiving an event marker therefrom. The event marker includes a timestamp. Based at least in part on the timestamp, the UI aligns an indication of the event marker to a representation of a heart signal on one of a display or a recording.

This document also describes, among other things, a method. The method includes observing the occurrence of an event associated with an implantable cardiac rhythm management device. The event is timestamped with a time that relates to the event's time of occurrence. The event marker which includes the timestamp, is transmitted to a remote user interface. The event marker is received at the remote user interface. A representation of the event marker is aligned in time, based at least in part on the timestamp, to a representation of a cardiac signal. The aligned event marker representation and cardiac signal representation are displayed, recorded, or stored. These and other aspects of the present system and methods will become apparent upon reading the following detailed description and viewing the accompanying drawings that form a part thereof.

BRIEF DESCRIPTION OF THE DRAWINGS

In the drawings, like numerals describe substantially similar components throughout the several views. Like numerals having different letter suffixes represent different instances of substantially similar components.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components. In this document, "and/or" refers to non-exclusive "or" (e.g., "A and/or B" includes each of "A but not B," "B but not A," and "A and B").

The present methods and apparatus will be described in applications involving implantable medical devices including, but not limited to, implantable cardiac rhythm management systems such as pacemakers, cardioverter/defibrillators, pacer/defibrillators, and biventricular or other multi-site coordination devices. However, it is understood that the present methods and apparatus may be employed in unimplanted devices, including, but not limited to, external pacemakers, cardioverter/defibrillators, pacer/defibrillators, biventricular or other multi-site coordination devices, monitors, programmers and recorders.

General System Overview and Examples

Figure 1:
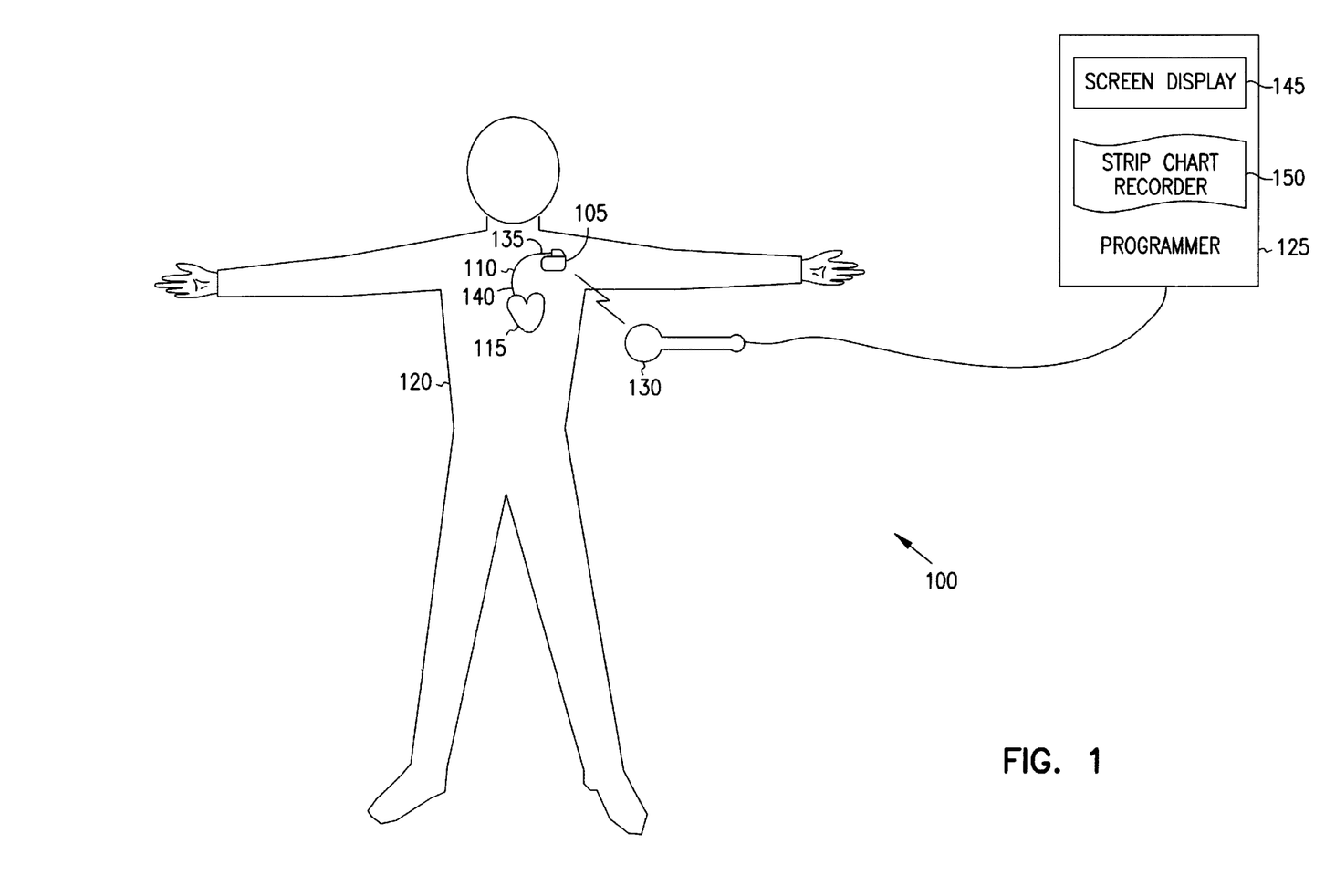
FIG. 1 is a schematic drawing illustrating generally one embodiment of portions of a cardiac rhythm management system and an environment in which it is used.

This document describes, among other things, a cardiac rhythm management system with event marker alignment by inclusion of event marker transmission latency in the real-time data stream. FIG. 1 is a schematic drawing illustrating generally, by way of example, but not by way of limitations one embodiment of portions of a cardiac rhythm management system 100 and an environment in which it is used. In FIG. 1, system 100 includes an implantable cardiac rhythm management device 105, also referred to as an electronics unit, which is coupled by an intravascular endocardial lead 110, or other lead, to a heart 115 of patient 120. System 100 also includes a user interface (UI), remote from device 105, such as an external programmer 125 providing wireless communication with device 105 using a telemetry device 130. Catheter lead 110 includes a proximal end 135, which is coupled to device 105, and a distal end 140, which is coupled to one or more positions of heart 115. Programmer 125 includes a screen display 145 and a printer such as strip chart recorder 150. System 100 may also include one or more surface electrocardiogram (ECG) skin electrodes, which are placed on the skin of patient 120 for receiving cardiac signals, and an associated cable for directly coupling the skin electrodes to programmer 125.

Figure 2:
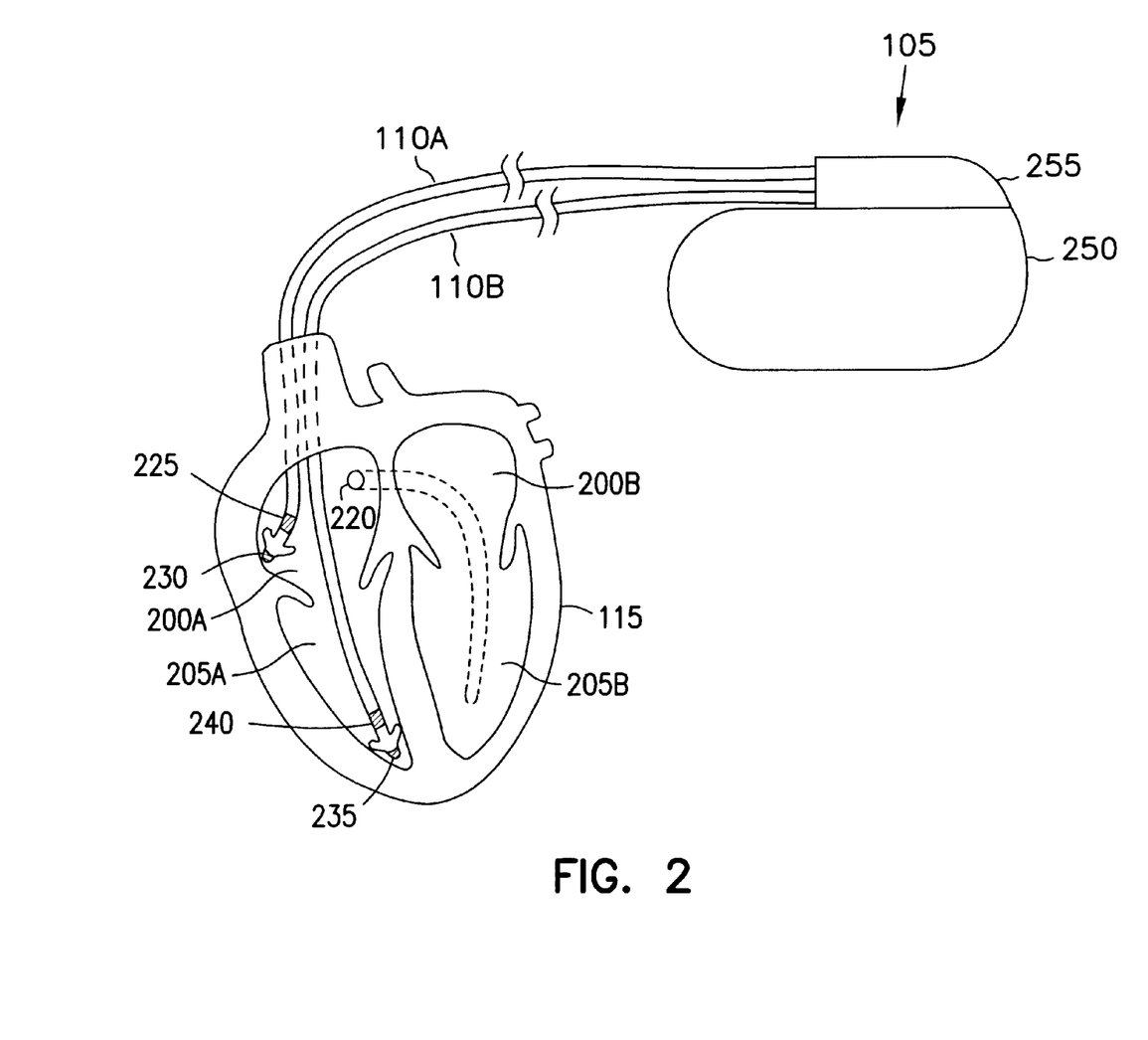
FIG. 2 is a schematic drawing illustrating generally one embodiment of a cardiac rhythm management device coupled by leads to a heart.

FIG. 2 is a schematic drawing illustrating generally, by way of example, but not by way of limitation, one embodiment of device 105 coupled by leads 110A–B to heart 115, which includes a right atrium 200A, a left atrium 200B, a light ventricle 205A, a left ventricle 205B, and a coronary sinus 220 extending from right atrium 200A. In this embodiment, atrial lead 110A includes electrodes (electrical contacts) disposed in, around, or near an atrium 200 of heart 115, such as ring electrode 225 and tip electrode 230, for sensing signals and/or delivering pacing therapy to the atrium 200. Lead 110A optionally also includes additional electrodes, such as for delivering atrial and/or ventricular cardioversion/defibrillation and/or pacing therapy to heart 115.

In FIG. 2, a ventricular lead 110B includes one or more electrodes, such as tip electrode 235 and ring electrode 240, for delivering sensing signals and/or delivering pacing therapy. Lead 110B optionally also includes additional electrodes, such as for delivering atrial and/or ventricular cardioversion/defibrillation and/or pacing therapy to heart 115. Device 105 includes components that are enclosed in a hermetically-sealed can 250. Additional electrodes may be located on the can 250, or on an insulating header 255, or on other portions of device 105, for providing unipolar pacing and/or defibrillation energy in conjunction with the electrodes disposed on or around heart 115. Other forms of electrodes include meshes and patches which may be applied to portions of heart 115 or which may be implanted in other areas of the body to help "steer" electrical currents produced by device 105. In one embodiment, one of atrial lead 110A or ventricular lead 110B is omitted, i.e., a "single chamber" device is provided, rather than the dual chamber device illustrated in FIG. 2. In another embodiment, additional leads are provided for coupling device 105 to other heart chambers and/or other locations in the same heart chamber as one or more of leads 110A–B. The present method and apparatus will work in a variety of configurations and with a variety of electrical contacts or "electrodes."

Example Cardiac Rhythm Management Device

Figure 3:
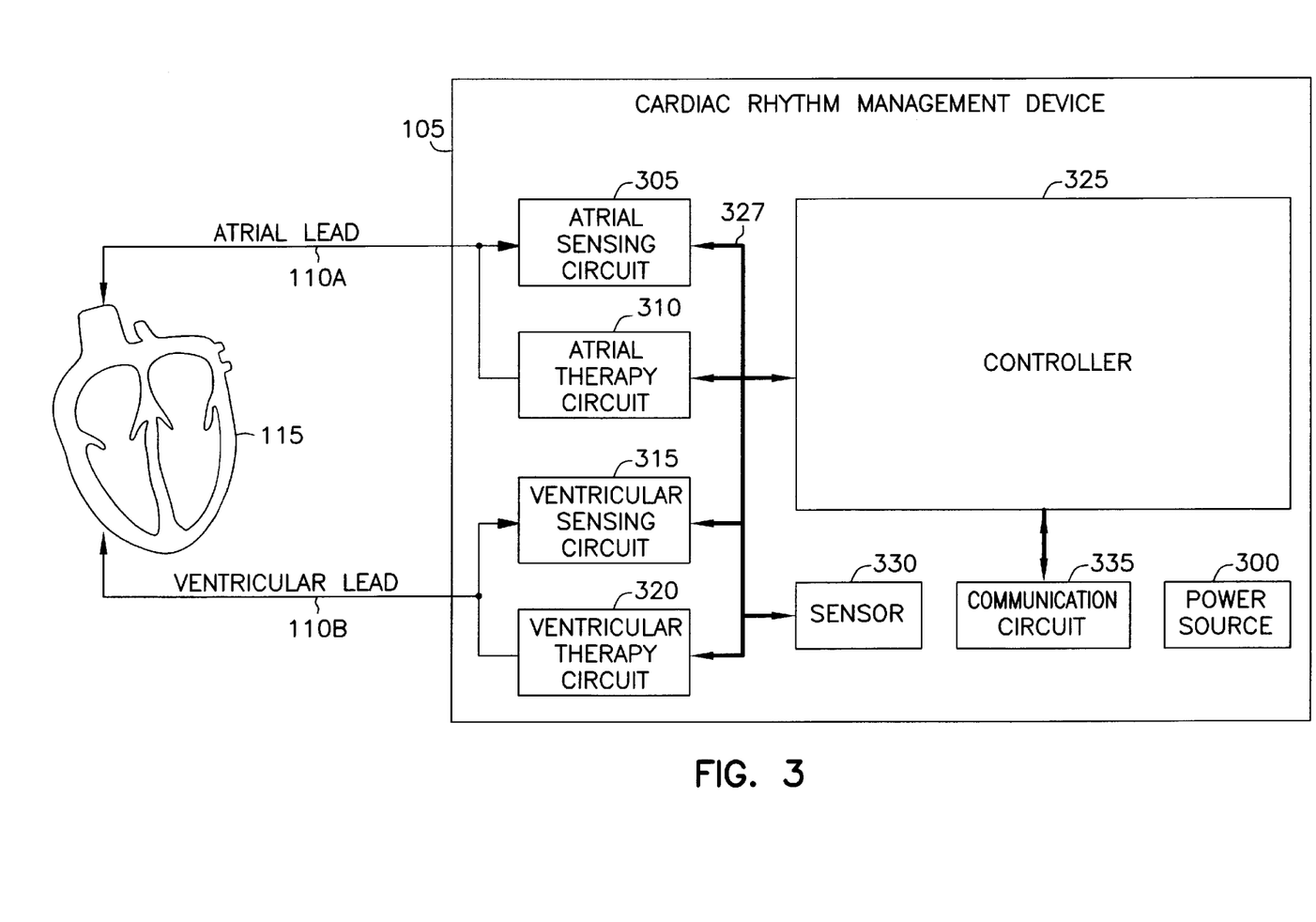
FIG. 3 is a schematic diagram illustrating generally one embodiment of portions of a cardiac rhythm management device, which is coupled to a heart, and certain aspects of the device.

FIG. 3 is a schematic diagram illustrating generally, by way of example, but not by way of limitation, one embodiment of portions of device 105, which is coupled to heart 115. Device 105 includes a power source 300, all atrial sensing circuit 305, an atrial therapy circuit 310 a ventricular sensing circuit 315, a ventricular therapy circuit 320, and a controller 325.

Atrial sensing circuit 305 is coupled by atrial lead 110A to heart 115 for receiving, sensing, and/or detecting electrical atrial heart signals. Such atrial heart signals include trial atrial activations (also referred to as atrial depolarizations or P-waves), which correspond to atrial contractions. Such atrial heart signals include normal atrial rhythms, and abnormal atrial rhythms including atrial tachyarrhythmias, such as atrial fibrillation, and other atrial activity. Atrial sensing circuit 305 provides one or more signals to controller 325, via node/bus 327, based on the received atrial heart signals.

In one embodiment, atrial therapy circuit 310 provides atrial pacing therapy, as appropriate, to electrodes located at or near one of the atria 200 of heart 115 for obtaining resulting evoked atrial depolarizations. In a further embodiment, atrial therapy circuit 310 also provides cardioversion/defibrillation therapy, as appropriate, to electrodes located at or near one of the atria 200 of heart 115, for terminating atrial fibrillation and/or other atrial tachyarrhythmias.

Ventricular sensing circuit 315 is coupled by ventricular lead 110B to heart 115 for receiving, sensing, and/or detecting electrical ventricular heart signals, such as ventricular activations (also referred to as ventricular depolarizations or R-waves), which correspond to ventricular contractions. Such ventricular heart signals include normal ventricular rhythms, and abnormal ventricular rhythms, including ventricular tachyarrhythmias, such as ventricular fibrillation, and other ventricular activity. Ventricular sensing circuit 315 provides one or more signals to controller 325, via node/bus 327, based on the received ventricular heart signals.

In one embodiment, ventricular therapy circuit 320 provides ventricular pacing therapy, as appropriate, to electrodes located at or near one of the ventricles 205 of heart 115 for obtaining resulting evoked ventricular depolarizations. In a further embodiment, ventricular therapy circuit 320 also provides cardioversion/defibrillation therapy, as appropriate, to electrodes located at or near one of the ventricles 205 of heart 115, for terminating ventricular fibrillation and/or other ventricular tachyarrhythmias.

Controller 325 controls the delivery of therapy by atrial therapy circuit and/or ventricular therapy circuit 320 and/or other circuits, based on heart activity signals received from atrial sensing circuit 305 and ventricular sensing circuit 315, as discussed below. Controller 325 includes various modules, which are implemented either in hardware or as one or more sequences of steps carried out on a microprocessor or other controller. Such modules are illustrated separately for conceptual clarity; it is understood that the various modules of controller 325 need not be separately embodied, but may be combined and/or otherwise implemented, such as in software/firmware.

In general terns, sensing circuits 305 and 315 sense electrical signals from heart tissue in contact with the catheter leads 110A–B to which these sensing circuits 305 and 315 are coupled. Sensing circuits 305 and 315 and/or controller 325 process these sensed signals. Based on these sensed signals, controller 325 issues control signals to therapy circuits, such as ventricular therapy circuit 320, if necessary, for the delivery of electrical energy (e.g., pacing and/or defibrillation pulses) to the appropriate electrodes of leads 110A–B. Controller 325; may include a microprocessor or other controller for execution of software and/or firmware instructions. The software of controller 325 may be modified (e.g., by remote external programmer 105) to provide different parameters, modes, and/or functions for the implantable device 105 or to adapt or improve performance of device 105.

In one further embodiment, one or more sensors, such as sensor 330, may serve as inputs to controller 325 for adjusting the rate at which pacing or other therapy is delivered to heat 115. One such sensor 330 includes an accelerometer that provides an input to controller 325 indicating increases and decreases in physical activity, for which controller 325 increases and decreases pacing rate, respectively. Another such sensor includes an impedance measurement, obtained from body electrodes, which provides an indication of increases and decreases in the patient's respiration, for example, for which controller 325 increases and decreases pacing rate, respectively. Any other sensor 330 providing an indicated pacing rate can be used. Device 105 also includes a communication circuit 335 for communication with telemetry device 130 of programmer 125.

Example Diagnostics Overview

Figure 4:
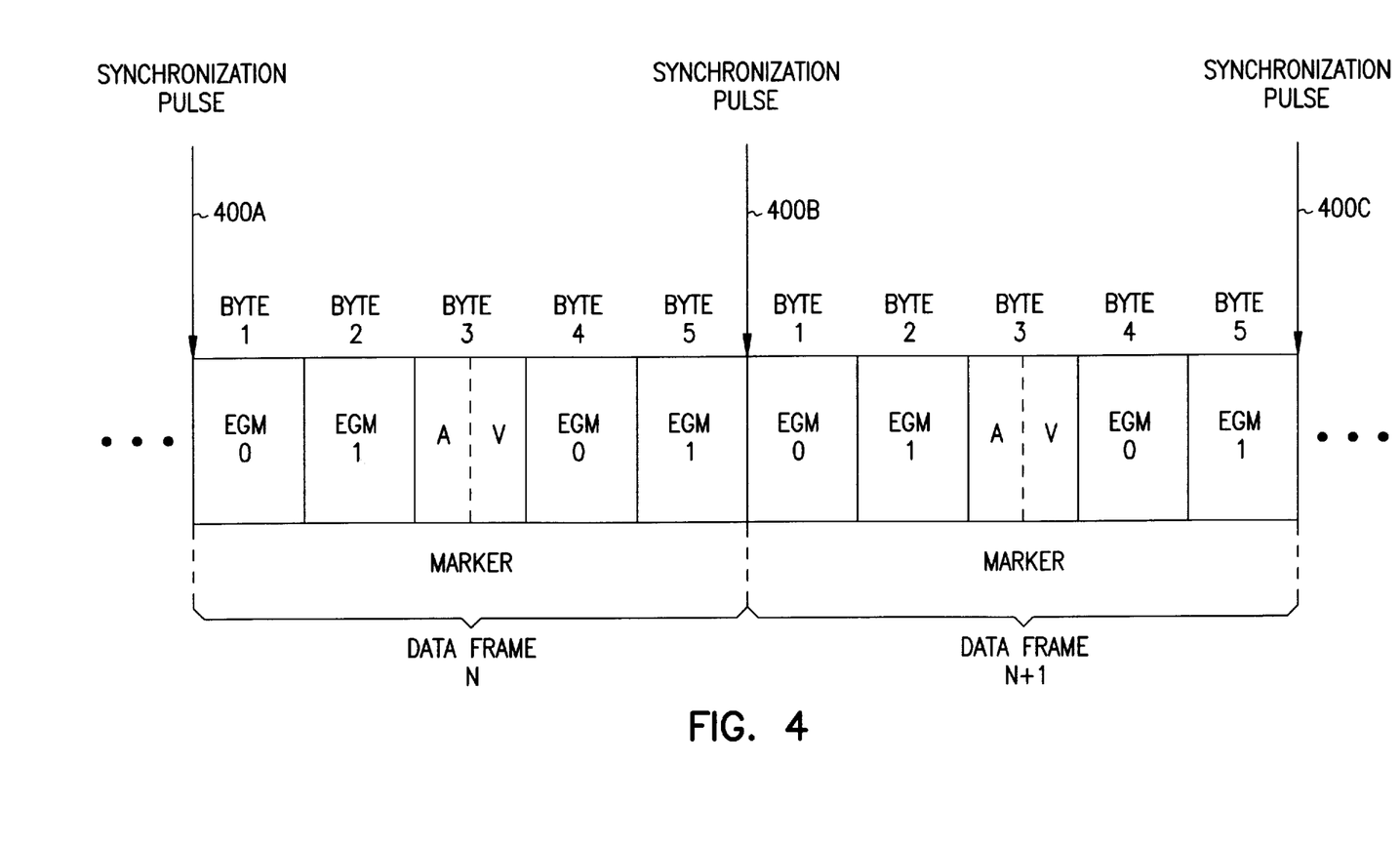
FIG. 4 illustrates generally one embodiment of a portion of a real-time data stream communicating diagnostic and/or other data from an implantable cardiac rhythm management device.

FIG. 4 illustrates generally, by way of example, but not by way of limitation, one embodiment of a portion of a real-time data stream communicating diagnostic and/or other data from device 105 to programmer 125 according to one example communication protocol during a real-time telemetry diagnostics mode. Programmer 125 processes and displays representations of such information on screen display 145, records representations of such information on a printed strip chart provided by strip chart recorder 150, and/or stores representations of such information in memory in programmer 125. In one particular embodiment, the displayed and/or recorded diagnostic data also includes an "ECG" representation of a cardiac signal obtained via one or more surface ECG electrodes, "electrogram" representations of cardiac signals obtained by implanted device 105, and representations of event markers that denote the occurrence of particular events associated with implanted device 105. Because the surface ECG signals are obtained directly from external skin electrodes coupled to programmer 125 using a cable, the surface ECG signal data is not telemetered from device 105 to programmer 125.

In FIG. 4, programmer 125 provides synchronization pulses ("sync pulses") 400 to device 105. Between successive synchronization pulses 400, device 105 communicates a frame of data to programmer 125. In this example, each data frame includes five bytes of data and is transmitted from device 105 to programmer 125 in approximately 8.3 milliseconds. Each data frame is divided into 6 data slots: (1) electrogram channel 0, (2) electrogram channel 1. (3) atrial event markers, (4) ventricular event markers, (5) electrogram channel 0 again, and (6) electrogram channel 1 again. Two different channels of electrogram data (channel 0 and channel 1) are transmitted from device 105 to programmer 125. In one example, these two channels are selected from any two of: (1) an atrial electrogram. (2) a ventricular electrogram, and (3) a shock lead electrogram. In this example, data associated with atrial event markers is transmitted at a rate of 4 bits per data frame. Similarly, data associated with ventricular event markers is also transmitted at this rate. Byte 3 includes both atrial and ventricular marker data. In this example, separate slots are available for atrial and ventricular event markers in each data frame.

Figure 5:
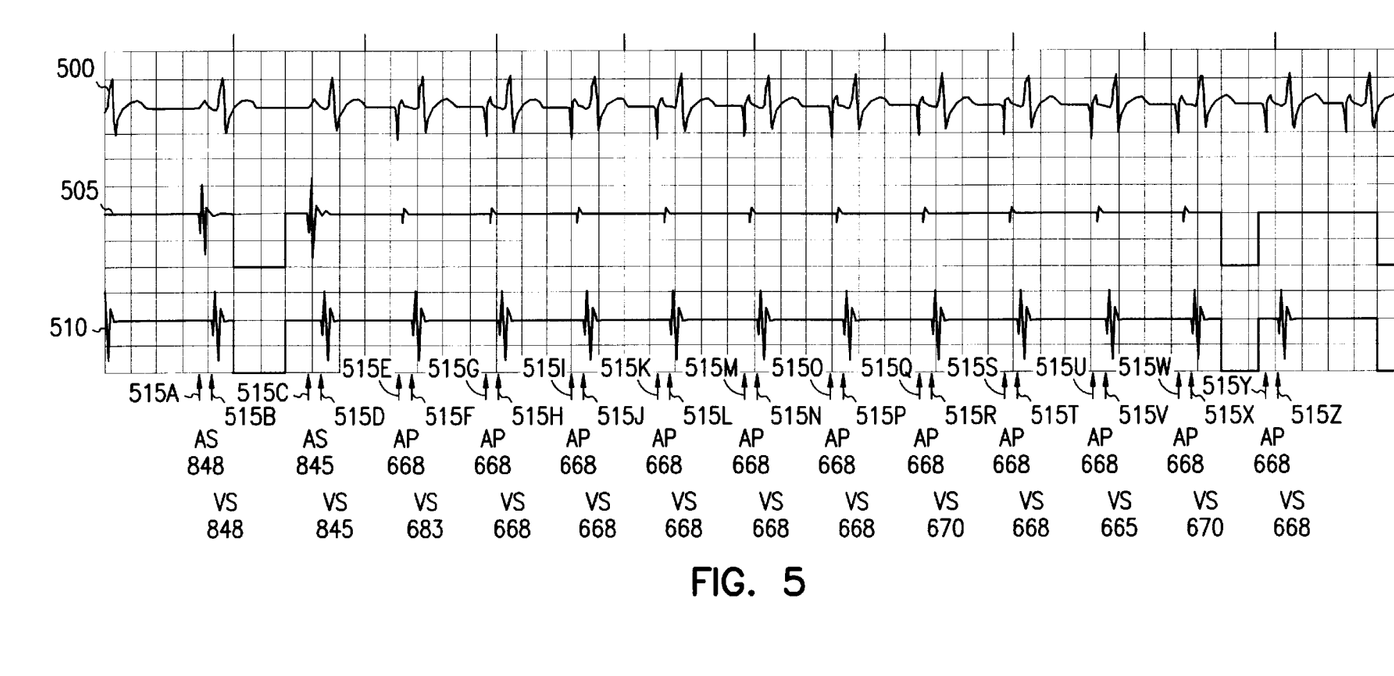
FIG. 5 is an example of a strip chart recording provided by a strip chart recorder associated with a user interface (UI) such as an external programmer that is included within the cardiac rhythm management system.

FIG. 5 is an example of a strip chart recording provided by strip chart recorder 150. Based at least in part on data telemetered from implanted device 105 to external programmer 125, the strip chart recording provides real-time electrograms of cardiac signals associated with one or more implanted or surface electrode sites. In the embodiment illustrated in FIG. 5, the strip chart includes cardiac signals from a surface ECG 500, an atrial electrogram 505, and a ventricular electrogram 510.

The strip chart of FIG. 5 also includes representations atrial and ventricular event markers 515A–Z, indicated by upwardly pointing arrows annotating the time associated with the event marker. These arrows indicate the occurrence of a pace, delivered by atrial therapy circuit 310 or ventricular therapy circuit 320, or of a sensed cardiac depolarization, detected by atrial sensing circuit 305 or ventricular sensing circuit 315. Below corresponding event markers, the strip chart includes text describing information related to the particular event marker. "AS" indicates that the associated event marker corresponds to all atrial sense, "AP" indicates that the associated event marker corresponds to an atrial pace. Similarly, "VS" indicates that the associated event marker corresponds to a ventricular sense, "VP" indicates that the associated event marker corresponds to a ventricular pace. A corresponding numeral indicates the time interval in milliseconds since the previous event marker in the same chamber. Although FIG. 5 is an example of a strip chart recording provided by strip chart recorder 150, it is understood that similar information is also displayed on screen display 145. It is also understood that many other types of event markers exist, indicating to the caregiver the presence of any event associated with implanted device 105. Such events may be entirely internal to implanted device 105, or may be associated with the sensing of heart signals or the delivery of pacing, defibrillation, and/or other therapy to the patient 120. Other marker types are identified by other text annotations. For normal markers, a corresponding numeral indicates the time interval in milliseconds since the previous event marker in the same chamber, as illustrated in FIG. 5. All this information is useful to the caregiver in diagnosing whether the implanted device is providing appropriate cardiac rhythm management therapy.

Each event marker typically includes enough data so that it takes several data frames for device 105 to completely transmit the information associated with a single event marker 515. In one example, a normal ventricular marker includes 8 bytes of information, while only 4 bits of ventricular event marker information can be transmitted per data frame, as illustrated in FIG. 4. In another example, a normal atrial marker includes 7 bytes of information while only 4 bits of atrial event marker information can be transmitted per data frame, as illustrated in FIG. 4. All the information in the normal event markers need not be displayed by screen display 145 or strip chart recorder 150. Some transmitted information may be used by programmer 125 for other purposes.

Because a normal event marker 515 takes longer than one frame to transmit, a transmission time delay exists between the occurrence of the event at device 105 and the receipt of the event marker 515 by programmer 125. However, to be useful to the caregiver, the event markers 515 must be displayed by screen display 145 and/or strip chart recorder 150 at the proper time relative to the surface ECG signal 500, atrial electrogram signal 505, and ventricular electrogram signal 515 that are also being displayed. Consequently the surface ECG signal 500 and electrogram signals 505 and 510 may be buffered and delayed by a fixed delay.

In one example, the fixed delay with which these heart signals are buffered is approximately equal to the longest transmission time delay between occurrence of the event at device 105 and receipt of the event marker by the programmer 125. For example, if the ventricular event marker includes the most information (e.g., 8 bytes), then it takes the most frames (e.g., 16 frames ) to transmit, resulting in the longest transmission time (e.g., 133 milliseconds). In this example, surface ECG signal 500 and electrogram signals 505 and 510 are buffered by a fixed delay of approximately 133 milliseconds. Event markers having a shorter transmission time than the fixed delay are received by programmer 125 and delayed by the difference between the transmission time of that shorter event marker and the fixed delay. This allows programmer 125 to "align" the event markers 515 in time relative to the surface ECG signal 500 and the electrogram signals 505 and 510 being displayed by screen display 145 and/or strip chart recorder 150.

Because of the large amount of information included in normal event markers 515, multiple events can occur in the same heart chamber during the transmission time of such normal event marker 515. If same chamber events are occurring faster than event markers 515 are being transmitted to programmer 125, then misalignment win occur even though the surface ECG signal 500 and electrograms 505 and 510 are being delayed by the fixed delay. This is because multiple same chamber events are occurring during the fixed delay, which corresponds only to the transmission time of a single event marker 515. Moreover, if events are occurring fast enough, it is possible that receipt of the event markers 515 continues to fall further behind so that the misalignment increases over time.

Because such erroneous diagnostic information may be more confusing, rather than helpful, to the caregiver as a result of these limitations on telemetry data communication, it may be desirable to use an abbreviated marker (also referred to as an "express marker"). An express marker includes less information than the "normal" or "full" marker, allowing it to be transmitted faster, i.e., with a shorter transmission time. In one example, the express marker omits the information regarding the exact time interval in milliseconds between event markers in the same heart chamber and also omits other information. In this example, the express marker includes only 2 bytes of data, needing only 4 data frames, or approximately 33 milliseconds to transmit, as compared with 133 milliseconds for a full ventricular marker and 117 milliseconds for a full atrial marker.

In one embodiment, device 105 automatically begins transmitting such express markers when multiple same-chamber events during the transmission of a full marker. Device 105 automatically resumes transmission of full markers when events begin to occur after a longer time than the transmission time of the last express marker.

Use of different types of markers (e.g., full and express) with different transmission times (e.g., long and short) can improve data throughout, but by itself it may, still result in problems in aligning the event markers 515 to the surface ECG signal 500 and electrogram signals 505 and 510. For example, the surface ECG signal 500 and electrogram signals 505 and 510 are typically delayed by a fixed delay that is equal to transmission time of a full ventricular marker (or other marker having the longest transmission time). As a result, a transmitted full ventricular marker will be properly aligned. A ventricular event occurring during transmission of this full ventricular marker, however, will be misaligned because transmission of the resulting express marker cannot begin until transmission of the previous full marker is completed.

Figure 6:
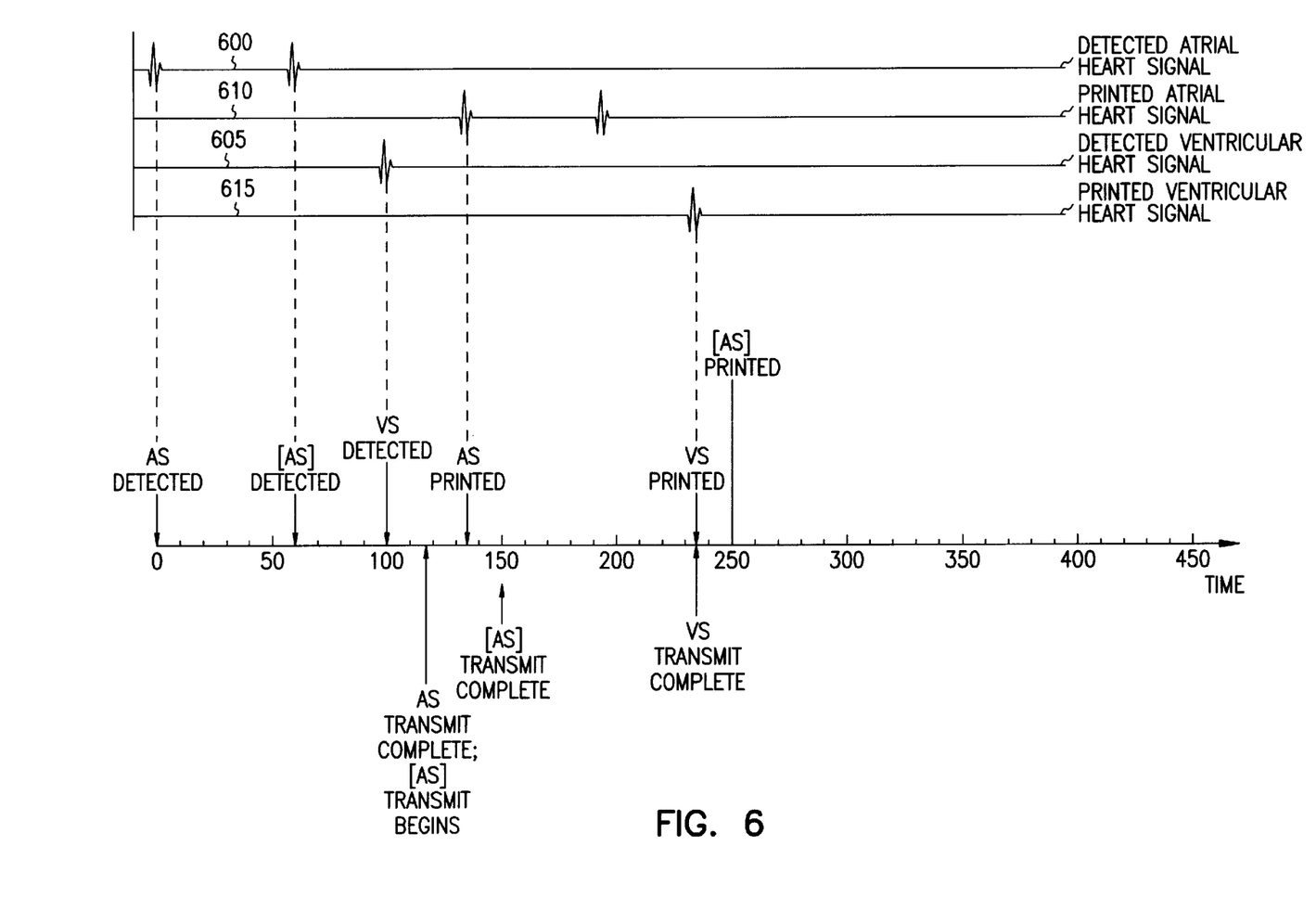
FIG. 6 illustrates generally one scenario of detected and printed/displayed electrograms and events, and underlying transmission times, in which misalignment of a printed/displayed event marker results.

FIG. 6 illustrates generally, by way of example, but not by way of limitation, one scenario in which misalignment results. FIG. 6 illustrates the atrial electrogram signal 600 and ventricular electrogram signal 605 detected by device 105. FIG. 6 also illustrates the printed/displayed representations atrial electrogram signal 610 and ventricular electrogram signal 615, each of which are buffered and delayed from the corresponding detected electrogram signals by approximately 133 milliseconds in this example. The surface ECG signal is omitted from FIG. 6 for clarity, however, the printed/displayed surface ECG signal would also be delayed from the detected ECG signal by 133 milliseconds in this example so that the printed/displayed ECG signal would be aligned to the printed/displayed electrogram signals 610 and 615.

In the scenario of FIG. 6, an atrial sense is detected at device 105 at time t=0 ms, triggering transmission of a full atrial marker which in this example takes 117 ms to transmit. At t=60 ms, another atrial sense is detected at device 105, which triggers transmission of an express atrial marker (denoted in FIG. 6 as [AS] to indicate it is an express marker) because it is detected during transmission of the previous full atrial marker. In this example, the express atrial marker requires only 33 ms to transmit, but its transmission cannot begin until transmission of the previous full atrial marker is complete at t=117 ms. At time t=100 ms, a ventricular sense is detected at device 105, triggering transmission of a full ventricular marker, which in this example takes 133 ms to transmit. Transmission of the full ventricular marker begins substantially immediately upon its detection, however, because separate data slots are available for atrial and ventricular markers, as illustrated in FIG. 4. In this embodiment, only if a ventricular sense is detected during the transmission of the previous ventricular marker will transmission of an express ventricular marker be triggered; detection of a ventricular sense during transmission of all atrial event marker does not result in switching the ventricular marker from full to express in this embodiment.

In FIG. 6, transmission of the full atrial marker begins at t=0 and ends at t=117 ms. Because this is shorter than the amount by which the electrograms 515 and surface ECG signal 500 are delayed (e.g., 133 ms fixed delay in this example, which corresponds to the transmission time of the longest marker, in this case a full ventricular marker), printing of the full atrial marker is delayed by the difference between the transmission time of the full atrial marker (e.g., 117 ms) and the fixed delay of the buffered heart signals (e.g., 133 ms). Thus, printing of the full atrial marker is delayed by another 16 ms after its transmission is completed at t=117 ms so that the full atrial marker is printed at t=133 ms. Because the transmission time of the full ventricular marker is equal to the fixed delay of the heart signals (e.g., 133 ms), no further delay is needed; the full ventricular marker is printed upon completion of its transmission at t=233 ms. Transmission of the express atrial marker begins upon completion of transmission of the previous full atrial marker at t=117 ms. Transmission of the express atrial marker takes approximately 33 ms and is completed at t=150 ms. Because the express atrial marker transmission time is shorter than fixed delay of the buffered heart signals of 133 ms printing of the express atrial marker is delayed by the difference between the transmission time of the express atrial marker (e.g., 33 ms) and the fixed delay of the buffered heart signals (e.g., 133 ms). Thus, printing of the express atrial marker is delayed by another 100 ms after its transmission is complete at t=150 ms, so that the express atrial marker is printed at t=250 ms, in this example.

In this scenario, because the express second atrial marker is improperly aligned and excessively delayed, it is displayed after the properly aligned marker associated with the first ventricular event. This is particularly misleading to the caregiver, because it suggests that the second atrial sense occurred after the first ventricular sense. In reality, these events occurred in the opposite order, as indicated by FIG. 6. The caregiver may erroneously conclude that the second atrial sense is not a true atrial sense, but instead represents far-field sensing of the first ventricular event by the atrial electrode. To resolve this perceived "problem" the caregiver may program the atrial sensing channel of the implanted device to a reduced sensitivity, or may decide that the atrial lead should be repositioned so that the atrial electrodes are located farther from the ventricular chamber of the heart. Both actions would be unfortunate, however, because the perceived problem does not exist; it is an artifact of limitations on the telemetry data communication and marker alignment protocols.

In order to resolve the problem illustrated in FIG. 6, the present cardiac rhythm management system 100 includes in the express marker data a timestamp so that programmer 125 can align the express marker by delaying printing of the express marker by a period of time that is based at least in part on the timestamp information included in the express marker data. In one embodiment, by way of example, but not by way of limitation, this timestamp relates to the time between the event underlying the express marker event and the event underlying the previous full marker. In FIG. 6, the time difference between the express atrial marker event and the full atrial marker event is timestamp=[(t=60 ms)–(t=0 ms)]=60 ms. This timestamp information is encoded and transmitted from device 105 to programmer 125 as part of the express marker.

Figure 7:
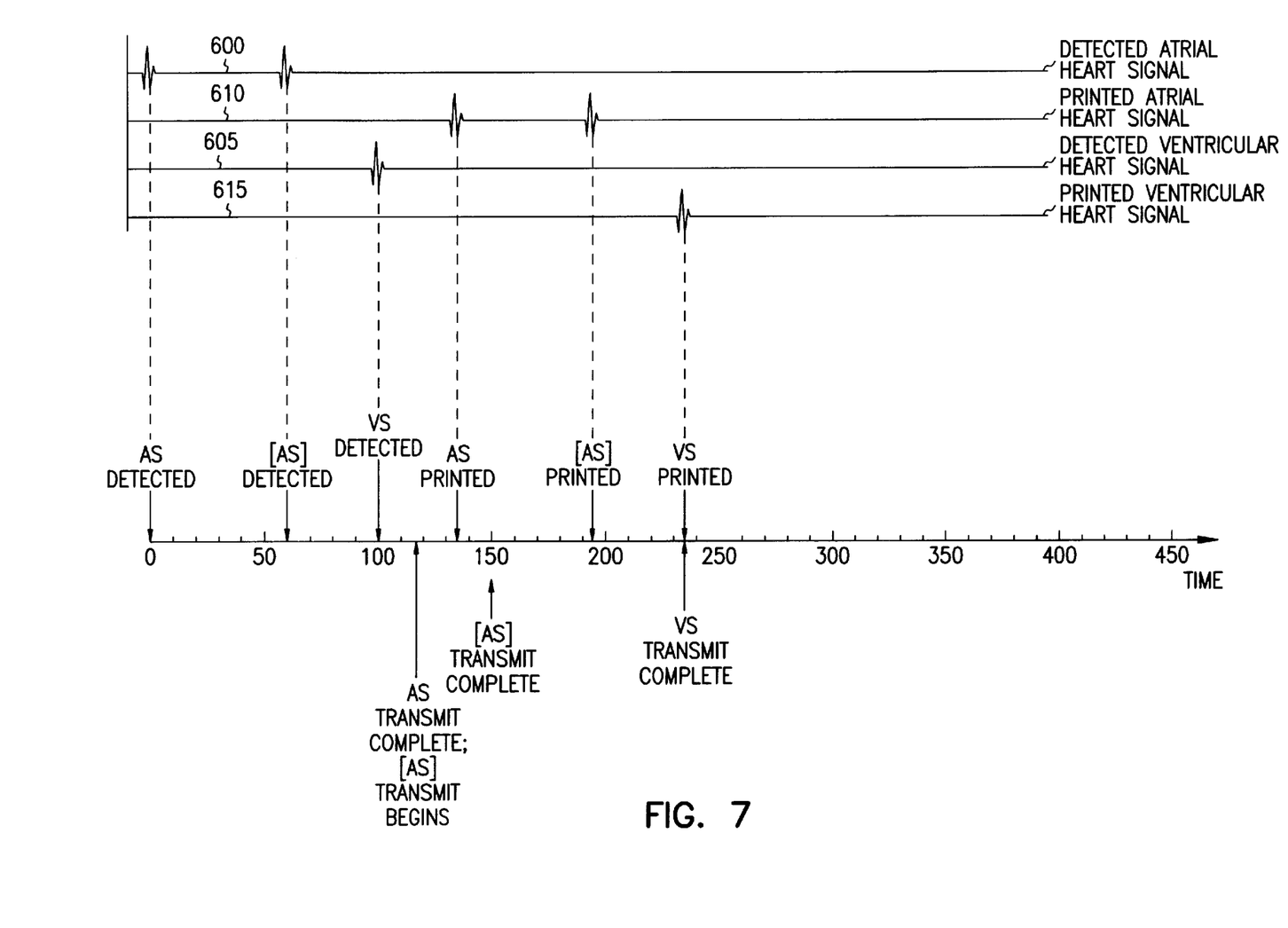
FIG. 7 illustrates generally the scenario of FIG. 6, in which timestamp information relating to the time of occurrence of an event is used to properly align the displayed or printed event marker so that no misalignment of the displayed/printed event marker results.

In one embodiment, programmer 125 calculates the time remaining in transmitting the full atrial marker after the express marker event. This time difference is calculated as the atrial transmission time (e.g., 117 ms) less the timestamp (e.g., 60 ms), yielding 57 ms in this example. The delay in printing/displaying the express marker is decreased by this amount to properly align the displayed/printed express marker with the displayed/printed heart signals. As discussed above, the fixed portion of the express marker delay is the fixed delay of the printed/displayed heart signals (e.g., 133 ms) less the transmission time of the express marker (e.g., 33 ms), or 100 ms in this example. The fixed portion of the express marker delay (e.g., 100 ms) is decreased by the time remaining during full marker transmission after the express marker event is detected (e.g., 57 ms), yielding 43 ms in this example. Thus, in this example, printing/displaying the express marker is delayed for 43 ms after its transmission is completed at t=150 ms, so that the express marker is printed at t=193 ms, which is properly aligned to the corresponding printed atrial sensed event, as illustrated in FIG. 7.

Figure 8:
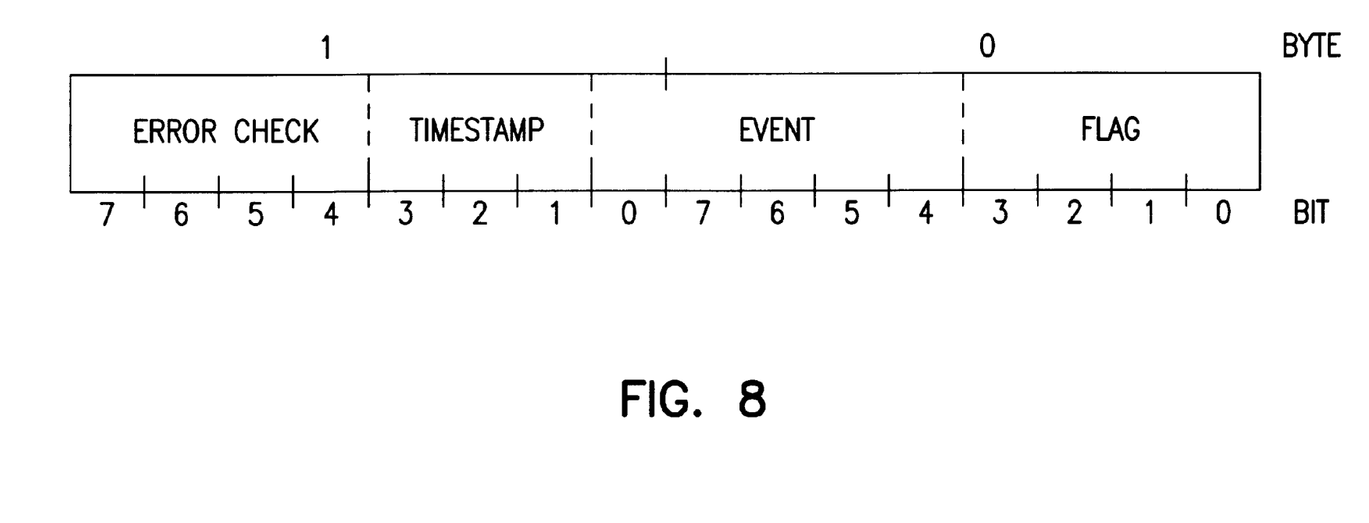
FIG. 8 illustrates generally one embodiment of a two byte express marker that includes timestamp information relating to the time of occurrence of an underlying event.

FIG. 8 illustrates generally, by way of example, but not by way of limitation one embodiment of a two byte express marker that includes the timestamp. In one embodiment, the two byte express marker is transmitted from device 105 to programmer 125 over four data frames for a transmission time of approximately 33 ms. In the example of FIG. 8, the two bytes of the express marker includes a 4 bit marker flag field, a 5 bit event code field, a 3 bit encoded timestamp) field, and a 4 bit error checking and/or error correction field ("error field "). The flag field includes information indicating that the data is a marker. In one embodiment, the flag field also includes information indicating the type of marker (e.g. express vs. full/normal). The event code field provides information regarding the kind of event being marked. The above discussion listed a few examples of different kinds of events (e.g., atrial sense, atrial pace, ventricular sense, ventricular pace) that are marked by event markers. However, it is understood that the occurrence of many other kinds of events may be communicated using event markers for printing/displayed or other use by programmer 125.

The timestamp field includes information relating to the time that the express marker's underlying event ("express marker event") occurred. In one embodiment, as described above, the timestamp represents the time between occurrence of the express marker event and occurrence of the previous full marker event for which a full marker is being transmitted. However this is not the only possible way of providing information relating to the time that the express marker occurred. In an alternate embodiment, for example, the timestamp represents the time between the occurrence of the express market event and the time at which transmission of the previous full marker is complete (and the timestamp is processed accordingly by programmer 125). Thus, the timestamp may include any convenient expression of information regarding the time at which the event underlying the express marker occurred.

In one embodiment, the timestamp field is limited to 3 bits of information to keep the express marker within two bytes. A longer express marker would require longer transmission. Increasing the transmission time increases the likelihood of multiple same chamber events occurring during the transmission. In one example, the timestamp information is encoded into a 3 bit count stored in the timestamp field. Each bit corresponds to approximately 20 ms. If one count value is reserved for representing zero delay, then the seven remaining counts in the 3 bits can encode delays of up to approximately 140 ms between the occurrence of the event underlying the express marker and the occurrence of the event underlying the previous full marker. This is sufficient to cover the full transmission time associated with a full ventricular marker (the longest full marker to transmit in the above example). Any other convenient coding arrangement may be used.

In the example illustrated in FIG. 8, only 4 bits are available for error checking and/or correction. In one embodiment, error checking is performed for the 8 bits of time stamp and event code data (but not for the flag data) using an 8.4 Hamming code. This allows the 8 bits of time stamp and event code data to be checked using only a 4 bit error checking value as illustrated in FIG. 8. Hamming codes are described in Andrew S. Tannenbaum, *Computer Networks,* 125–28 (Prentice-Hall 1981), which is incorporated herein by reference.

CONCLUSION

This document describes, among other things, portions of a cardiac rhythm management system transmitting event markers from all implantable device to a remote user interface, in which the event markers include timestamp information upon which alignment of a printed/displayed event marker representation to a printed/displayed heart signal representation is based at least in part. Proper alignment of the printed/displayed heart signal representation to the printed/displayed event marker, and proper alignment of the printed/displayed event markers with respect to each other, provides more accurate diagnostic information to the caregiver. This assists the caregiver in using the cardiac rhythm management system to provide a patient with proper cardiac rhythm management therapy.

Although examples of the invention are described above with respect to a particular application in a cardiac rhythm management system, the present techniques could be applied in any other data communication application that requires alignment of data because of delays in data transmission. Moreover, although the above example particularly described aligning the printed/displayed express markers to a printed/displayed heart signal based at least in part on timestamp information included in the express marker, it is understood that the present techniques to aligning printed/displayed full/normal markers to a printed/displayed heart signal based at least in part on timestamp information included in the full/normal markers. As discussed above, full/normal markers typically do include information about the time since the previous event in the same chamber. Furthermore, event markers are not limited only to sensed and paced event markers, but relate to any kind of event or data associated with the implanted device. Still further, the timestamp included in the event marker includes any kind of information relating to the time of occurrence of the event associated with the event marker, and includes times that describe the relationship between the time of the event and the time of other events.

It is to be understood that the above description is intended to be illustrative, and not restrictive. Many other embodiments will be apparent to those of skin in the art upon reviewing the above description. The scope of the invention should, therefore, be determined with reference to the appended claims, along with the full scope of equivalents to which such claims are entitled.

What is claimed is:

1. A cardiac rhythm management system, including:
   an implantable cardiac rhythm management (CRM) device; and
   a user interface (UI), remote from the CRM device, the user interface adapted to be communicatively coupled to the CRM device for receiving a substantially real-time event marker and a substantially real-time electrogram therefrom, in which the event marker includes a timestamp relating at least in part to an approximate time between an event associated with the event marker and another event associated with another event marker, and based at least in part on the timestamp, the UI aligns an indication of the event marker to a substantially real-time representation of a heart signal on one of a display or a recording.

2. The system of claim 1, in which the heart signal is based on at least one of an electrogram signal communicated from the CRM device and a surface ECG signal.

3. The system of claim 1, in which the UI also aligns the indication of the event marker to the representation of the electrogram signal based on a fixed delay.

4. The system of claim 3, in which the event marker is one of a plurality of types of event markers, in which at least one type of event marker has a different transmission time from at least one other type of event marker.

5. The system of claim 4, in which the fixed delay is based on the longest transmission time among all of the types of event markers.

6. The system of claim 1 in which the UI is adapted to receive data from the CRM device in frames, in which each data frame includes a plurality of data slots including:
   a first data slot associated with a first event marker associated with a first electrode; and
   a second data slot associated with a second event marker associated with a second electrode different from the first electrode.

7. The system of claim 6, in which at least one event marker requires more than one data frame for transmission of the event marker from the CRM device to the UI.

8. The system of claim 7, in which a first type of event marker includes an express event marker including at least two bytes of data, and a second type of event marker includes a full event marker including more bytes of data than the express event marker.

9. The system of claim 8, in which the express event marker includes a Hamming code error correction field.

10. The system of claim 1, in which the timestamp relates at least in part to an approximate time between the an event associated with the event marker and another event associated with another event marker.

11. The system of claim 1 in which the timestamp relates at least in part to an approximate time between an event associated with the event marker and another event associated with a previous event marker associated with the same electrode.

12. The system of claim 1, in which the timestamp relates at least in part to an approximate time between an event associated with the event marker and another event associated with a previous event marker associated with the same heart chamber.

13. The system of claim 1, in which the timestamp relates at least in part to all approximate time between an event associated with the event marker and the transmission completion time associated with a previous event marker associated with the same heart chamber.

14. A cardiac rhythm management system, including:
   an atrial lead, including at least one atrial electrode;
   a ventricular lead, including at least one ventricular electrode;
   an implantable cardiac rhythm management (CRM) device; and
   an external programmer, including a screen display and a strip chart recorder, the programmer adapted to be communicatively coupled to the CRM device for receiving frames of data therefrom, each data frame including:
   at least one first channel electrogram data slot;
   at least one second channel electrogram data slot;
   an atrial event marker data slot, for transmitting a first atrial event marker having a first transmission time and a second atrial event marker having a second transmission time different from the first transmission time, the second atrial event marker including a flag field, an event code field, a timestamp field, and a Hamming-coded error correction field;
   a ventricular event marker data slot, for transmitting a first ventricular event marker having a third transmission time and a second ventricular event marker having a fourth transmission time different from the third transmission time, the second atrial event marker including a flag field, an event code field, a timestamp field, and a Hamming-coded error correction field; and
   in which the programmer aligns, on one of the display or the recorder, indications of the atrial and ventricular event markers to at least one of (a) an electrogram representation or (b) a surface electrocardiogram (ECG) representation, and in which the alignment of event markers is based on the associated timestamps and a fixed delay corresponding to the longest transmission time of the event markers, and in which at least one event marker requires more than one data frame for transmission of the event marker from the CRM device to the external programmer, and in which the timestamp field in the atrial and ventricular event markers relates to an approximate time between the event marker and a previous event marker associated with the same heart chamber.

15. The system of claim 14, further including at least one shock electrode, and in which the first and second electrogram data slots provide electrogram signal data associated with two electrodes selected from the group consisting of: the atrial electrode, the ventricular electrode, and the shock electrode.

16. A method, including:
   observing the occurrence of an event associated with an implantable cardiac rhythm management device;
   timestamping the event with a time that relates to the event's time of occurrence;
   transmitting a substantially real-time electrogram and an event marker, which includes the timestamp, to a remote user interface, wherein the timestamp relates at least in part to an approximate time between an event associated with the event marker and another event associated with another event marker;
   receiving the electrogram and the event marker at the remote user interface;
   aligning in time, based at least in part on the timestamp, a representation of the event marker to a substantially real-time representation of a cardiac signal; and
   displaying, recording, or storing the aligned event marker representation and cardiac signal representation.

17. The method of claim 16, in which the timestamping the event is carried out relative to an occurrence of an earlier event.

18. The method of claim 16, in which the timestamping the event is carried out relative to a transmission completing time of a previous event marker being transmitted at the event's time of occurrence.

19. The method of claim 16, in which the aligning in time is also based on a fixed delay.

20. The method of claim 19, in which the aligning in time is also based on a fixed delay associated with a transmission time of an event marker.

21. The method of claim 20, in which the transmission and receiving the event marker includes transmitting and receiving a plurality of types of event markers, at least one type of event marker having a transmission time that is different from one other type of event marker.

22. The method of claim 21, in which the aligning in time is also based on a fixed delay associated with a longest transmission time of the different types of event markers.

23. The method of claim 16, it which the transmitting the event marker is carried out over a plurality of data frames.

24. The method of claim 16, in which transmitting the event marker includes coding at least a portion of the event marker with a Hamming code error checking field included in the event marker.

25. A method, including:
   receiving first and second channel electrogram data associated with first and second electrodes associated with all implantable cardiac rhythm management device;
   observing the occurrence of a first event associated with the first electrode;
   transmitting a first event marker from the device based on the occurrence of the first event;
   observing, during the transmitting of the first event marker, the occurrence of a second event associated with the first electrode;
   timestamping a second event marker with information relating to the time between the first and second events;
   receiving the first event marker at a remote user interface (UI);
   transmitting the second event marker, which includes the timestamp, to a remote UI after completion of the transmission of the first event marker;
   receiving the second event marker at the remote UI;
   aligning in time, based at least in part on the timestamp, a representation of the second event marker to a representation of a cardiac signal; and
   displaying, recording, or storing the aligned second event marker representation and the cardiac signal representation.

26. A cardiac rhythm management system, including:
   an implantable cardiac rhythm management (CRM) device; and
   a user interface (UI), remote from the CRM device, the user interface adapted to be communicatively coupled to the CRM device for receiving a substantially real-time event marker therefrom, in which the event marker includes a timestamp relating at least in part to an approximate time between an event associated with the event marker and another event associated with another event marker, and based at least in part on the timestamp, the UI aligns an indication of the event marker to a substantially real-time representation of a heart signal on one of a display or a recording, and in which the UI also aligns the indication of the event marker to the representation of the electrogram signal based on a fixed delay.

27. The system of claim 26, in which the event marker is one of a plurality of types of event markers, in which at least one type of event marker has a different transmission time from at least one other type of event marker.

28. The system of claim 27, in which the fixed delay is based on the longest transmission time among all of the types of event markers.

29. A cardiac rhythm management system, including:
   an implantable cardiac rhythm management (CRM) device; and
   a user interface (UI), remote from the CRM device, the user interface adapted to be communicatively coupled to the CRM device for receiving a substantially real-time event marker therefrom, in which the event marker includes a timestamp relating at least in part to an approximate time between an event associated with the event marker and another event associated with another event marker, and based at least in part on the timestamp, the UI aligns an indication of the event marker to a substantially real-time representation of a heart signal on one of a display or a recording, and in which the UI is adapted to receive data from the CRM device in frames, in which each data frame includes a plurality of data slots including:
   a first data slot associated with a first event marker associated with a first electrode; and
   a second data slot associated with a second event marker associated with a second electrode different from the first electrode.

30. The system of claim 29, in which at least one event marker requires more than one data frame for transmission of the event marker from the CRM device to the UI.

31. The system of claim 30, in which a first type of event marker includes an express event marker including at least two bytes of data, and a second type of event marker includes a full event marker including more bytes of data than the express event marker.

32. The system of claim 31, in which the express event marker includes a Hamming code error correction field.

33. A cardiac rhythm management system, including:
- an implantable cardiac rhythm management (CRM) device; and
- a user interface (UI), remote from the CRM device, the user interface adapted to be communicatively coupled to the CRM device for receiving a substantially real-time event marker therefrom, in which the event marker includes a timestamp relating at least in part to an approximate time between an event associated with the event marker and another event associated with another event marker, and based at least in part on the timestamp, the UI aligns an indication of the event marker to a substantially real-time representation of a heart signal on one of a display or a recording, and in which the timestamp relates at least in part to an approximate time between an event associated with the event marker and the transmission completion time associated with a previous event marker associated with the same heart chamber.

34. A method, including:
- observing the occurrence of an event associated with an implantable cardiac rhythm management device;
- timestamping the event with a time that relates to the event's time of occurrence, in which the timestamping the event is carried out relative to a transmission completion time of a previous event marker being transmitted at the event's time of occurrence;
- transmitting an event marker, which includes the timestamp, to a remote user interface, wherein the timestamp relates at least in part to an approximate time between an event associated with the event marker and another event associated with another event marker;
- receiving the event marker at the remote user interface;
- aligning in time, based at least in part on the timestamp, a representation of the event marker to a substantially real-time representation of a cardiac signal; and
- displaying, recording, or storing the aligned event marker representation and cardiac signal representation.

35. The method of claim 34, in which the aligning in time is also based on a fixed delay.

36. The method of claim 35, in which the aligning in time is also based on a fixed delay associated with a transmission time of an event marker.

37. The method of claim 36, in which the transmitting and receiving the event marker includes transmitting and receiving a plurality of types of event markers, at least one type of event marker having a transmission time that is different from one other type of event marker.

38. The method of claim 37, in which the aligning in time is also based on a fixed delay associated with a longest transmission time of the different types of event markers.

39. A method, including:
- observing the occurrence of an event associated with an implantable cardiac rhythm management device;
- timestamping the event with a time that relates to the event's time of occurrence, in which the transmitting the event marker is carried out over a plurality of data frames;
- transmitting an event marker, which includes the timestamp, to a remote user interface, wherein the timestamp relates at least in part to an approximate time between an event associated with the event marker and another event associated with another event marker;
- receiving the event marker at the remote user interface;
- aligning in time, based at least in part on the timestamp, a representation of the event marker to a substantially real-time representation of a cardiac signal; and
- displaying, recording, or storing the aligned event marker representation and cardiac signal representation.

40. A method, including:
- observing the occurrence of an event associated with an implantable cardiac rhythm management device;
- timestamping the event with a time that relates to the event's time of occurrence;
- transmitting an event marker, which includes the timestamp, to a remote user interface, wherein the timestamp relates at least in part to an approximate time between an event associated with the event marker and another event associated with another event marker, in which transmitting the event marker includes coding at least a portion of the event marker with a Hamming code error checking field included in the event marker;
- receiving the event marker at the remote user interface;
- aligning in time, based at least in part on the timestamp, a representation of the event marker to a substantially real-time representation of a cardiac signal; and
- displaying, recording, or storing the aligned event marker representation and cardiac signal representation.

* * * * *

UNITED STATES PATENT AND TRADEMARK OFFICE
CERTIFICATE OF CORRECTION

PATENT NO. : 6,535,763 B1  
DATED : March 18, 2003  
INVENTOR(S) : James F. W. Hiebert, Howard D. Simms Jr. and Allan T. Koshiol It is certified that error appears in the above-identified patent and that said Letters Patent is hereby corrected as shown below:

Title page,
Item [73], Assignee, delete "Cardia" and insert -- Cardiac -- therefor.
Item [74], insert -- , -- between "Schwegman" and "Lundberg".
Item [57], ABSTRACT,
Line 8, insert -- , -- after "marker".

Column 14,
Line 9, delete "the" after "between".
Line 12, insert -- , -- after "claim 1".

Column 15,
Line 57, delete "all" and insert -- an -- therefor.

Signed and Sealed this

Twelfth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,535,763 B1
DATED : March 18, 2003
INVENTOR(S) : James F. Hiebert, Howard D. Simms, Jr. and Allan T. Koshiol It is certified that error appears in the above-identified patent and that said Letters Patent is hereby corrected as shown below:

Column 2,
Line 28, delete "chair" and insert -- chart -- therefor.

Column 3,
Line 29, delete ")" after "timestamp".

Column 9,
Line 17, delete "win" and insert -- will -- therefor.
Line 50, delete "throughout" and insert -- throughput -- therefor.

Column 13,
Line 22, delete "skin" and insert -- skill -- therefor.
Line 57, insert -- , -- after "claim 1".

Signed and Sealed this

Twenty-fifth Day of November, 2003

JAMES E. ROGAN
*Director of the United States Patent and Trademark Office*